(12) United States Patent
Jones et al.

(10) Patent No.: US 9,220,846 B2
(45) Date of Patent: Dec. 29, 2015

(54) MEDICATED MODULE FOR AN OPHTHALMIC DRUG DELIVERY DEVICE

(75) Inventors: Christopher John Jones, Tewkesbury (GB); Carmen Patricia Keating, Aspley (AU); Daniel Thomas De Sausmarez Lintell, Rugby (GB); David Aubrey Plumptre, Droitwich Spa (GB); Malcolm Stanley Boyd, Wellesbourne (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 136 days.

(21) Appl. No.: 13/885,823

(22) PCT Filed: Nov. 28, 2011

(86) PCT No.: PCT/EP2011/071129
§ 371 (c)(1),
(2), (4) Date: May 16, 2013

(87) PCT Pub. No.: WO2012/072553
PCT Pub. Date: Jun. 7, 2012

(65) Prior Publication Data
US 2013/0261556 A1    Oct. 3, 2013

Related U.S. Application Data

(60) Provisional application No. 61/433,788, filed on Jan. 18, 2011.

(30) Foreign Application Priority Data

Nov. 26, 2010    (EP) .................................... 10192844

(51) Int. Cl.
*A61M 5/00*    (2006.01)
*A61M 5/315*    (2006.01)
(Continued)

(52) U.S. Cl.
CPC ............. *A61M 5/31545* (2013.01); *A61M 5/19* (2013.01); *A61M 5/3156* (2013.01);
(Continued)

(58) Field of Classification Search
CPC ............. A61M 2005/1787; A61M 2005/2474; A61M 5/19; A61M 5/20; A61M 5/24; A61M 5/31545; A61M 5/31551; A61M 5/3156; A61M 5/31585; A61M 5/31546; A61M 5/31548; A61M 5/3155; A61M 5/31553
See application file for complete search history.

(56) References Cited

U.S. PATENT DOCUMENTS 5,253,785 A    10/1993    Haber et al.
5,378,233 A    1/1995    Haber et al.
(Continued)

FOREIGN PATENT DOCUMENTS

DE    19930631    1/2001
WO    94/22507    10/1994

OTHER PUBLICATIONS

International Search Report and Written Opinion for Int. App. No. PCT/EP2011/071129, completed Jan. 5, 2012.
(Continued)

*Primary Examiner* — Rebecca E Eisenberg
(74) *Attorney, Agent, or Firm* — McDonnell Boehnen Hulbert & Berghoff LLP

(57) ABSTRACT

A drug delivery device having a collar and a linkage component. The drug delivery device includes a variable dose setting mechanism, a fixed dose setting mechanism, a single dose setter, a collar, and a linkage component. The variable dose setting mechanism is operably coupled to a primary reservoir holding a first medicament. The fixed dose setting mechanism is operably coupled to a secondary reservoir holding a second medicament. Further, the single dose setter is operably coupled to the variable dose setting mechanism, and the collar is disposed on the variable dose setting mechanism. Still further, the linkage component is disposed on the fixed dose setting mechanism, wherein the linkage component is capable of engagement with the collar.

15 Claims, 12 Drawing Sheets

(51) Int. Cl.
*A61M 5/19* (2006.01)
*A61M 5/20* (2006.01)
*A61M 5/24* (2006.01)
*A61M 5/34* (2006.01)
*A61M 5/178* (2006.01)

(52) U.S. Cl.
CPC ...... *A61M 5/31511* (2013.01); *A61M 5/31551* (2013.01); *A61M 5/31561* (2013.01); *A61M 5/31585* (2013.01); *A61M 5/002* (2013.01); *A61M 5/20* (2013.01); *A61M 5/2033* (2013.01); *A61M 5/2053* (2013.01); *A61M 5/24* (2013.01); *A61M 5/34* (2013.01); *A61M 2005/1787* (2013.01); *A61M 2005/208* (2013.01); *A61M 2005/2013* (2013.01); *A61M 2005/2474* (2013.01)

(56) References Cited

U.S. PATENT DOCUMENTS

2004/0011816 A1    1/2004   Muhlbauer et al.
2007/0060894 A1*   3/2007   Dai et al. ............... 604/207
2009/0264831 A1   10/2009   Thompson et al.

OTHER PUBLICATIONS

International Preliminary Report on Patentability for Int. App. No. PCT/EP2011/071129, mailed Jun. 13, 2013.

* cited by examiner

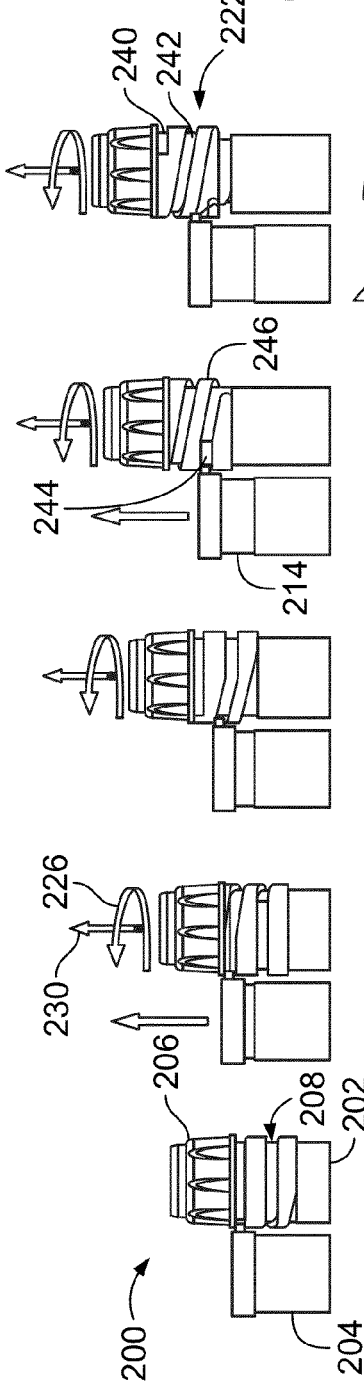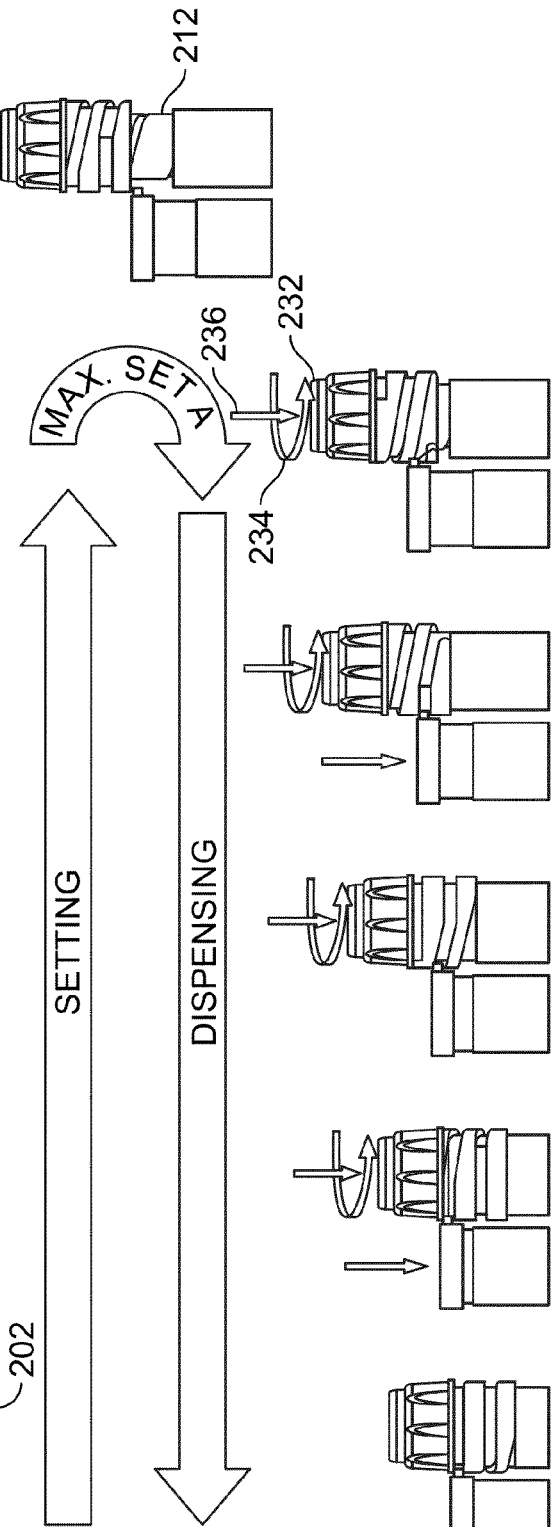

MEDICATED MODULE FOR AN OPHTHALMIC DRUG DELIVERY DEVICE

CROSS REFERENCE TO RELATED APPLICATIONS

The present application is a U.S. National Phase Application pursuant to 35 U.S.C. §371 of International Application No. PCT/EP2011/071129 filed Nov. 28, 2011, which claims priority to European Patent Application No. 10192844.8 filed Nov. 29, 2010 and U.S. Provisional Patent Application No. 61/433,788, filed Jan. 18, 2011. The entire disclosure contents of these applications are herewith incorporated by reference into the present application.

FIELD OF DISCLOSURE

This present patent application relates to drug delivery devices and methods of delivering at least two drug agents from separate reservoirs using devices having only a single dispense interface. The drug agents are contained in two or more multiple dose reservoirs, containers or packages, each containing independent (single drug compound) or pre-mixed (co-formulated multiple drug compounds) drug agents. The disclosed method and system is of particular benefit where the therapeutic response can be optimized for a specific target patient group, through control and definition of the therapeutic profile.

BACKGROUND

Certain disease states require treatment using one or more different medicaments. Some drug compounds need to be delivered in a specific relationship with each other in order to deliver the optimum therapeutic dose. The disclosed method and system is of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two active medicaments or "agents" simultaneously. The two active agents may interact with each other during the long-term, shelf life storage of the formulation. Therefore, it is advantageous to store the active components separately and only combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example, one or more actives may require a titration period to gradually introduce a patient to a "maintenance" dose. A further example would be if one active requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional problems may arise where a multi-drug compound therapy is required, because certain users cannot cope with having to use more than one drug delivery system or make the necessary accurate calculation of the required dose combination. This is especially true for users with dexterity or computational difficulties.

Accordingly, there exists a strong need to provide devices and methods for the delivery of two or more medicaments in a single injection or delivery step that is simple for the user to perform. The disclosed method and system overcomes the above-mentioned problems by providing separate storage containers for two or more active drug agents that are then only combined and/or delivered to the patient during a single delivery procedure. Setting a dose of one medicament automatically fixes or determines the dose of the second medicament (i.e. non-user settable).

The disclosed method and system also gives the opportunity for varying the quantity of one or both medicaments. For example, one fluid quantity can be varied by changing the properties of the injection device (e.g. dialing a user variable dose or changing the device's "fixed" dose). The second fluid quantity can be changed by manufacturing a variety of secondary drug containing packages with each variant containing a different volume and/or concentration of the second active agent. The user or healthcare professional would then select the most appropriate secondary package or series or combination of series of different packages for a particular treatment regime. Alternatively, the second fluid quantity can be changed by varying the properties of the fixed dose mechanism, such as a linkage component dispose on a fixed dose setting mechanism. The disclosed system and method may achieve a wide variety of target therapeutic profiles. For example, the disclosed system and method may achieve a therapeutic dose profile that delivers a fixed dose of a secondary medicament once a minimum setting threshold dose of a primary medicament has been set. As another example, the disclosed system and method may achieve a stepped fixed dose profile. The disclosed system and method also may add an element of auto-assistance that reduces the dispense force for the injection of two (or more) drug compounds while allowing the user a degree of control over the dispense process.

These and other advantages will become evident from the following more detailed description of the invention.

SUMMARY

The disclosed system and method allows complex combination of multiple drug compounds within a single device. In particular, the disclosed system and method allows the user to set and dispense a multi-drug compound device through a single dose setter and a single dispense interface. The drug delivery system includes a variable dose setting mechanism and a fixed dose setting mechanism. The system also includes a collar disposed on the variable dose setting mechanism and a linkage component disposed on the fixed dose setting mechanism, where the linkage component is capable of engagement with the collar. In an example, the single dose setter controls the dose setting mechanisms of the device such that a predefined combination of the individual drug compounds is delivered when a single minimum dose of one of the medicaments is set and dispensed through the single dispense interface.

By defining the therapeutic relationship between the individual drug compounds, Applicants' delivery device would help ensure that a patient/user receives the optimum therapeutic combination dose from a multi-drug compound device without the inherent risks associated with multiple inputs, where the user has to calculate and set the correct dose combination every time they use the device. The medicaments can be fluids, defined herein as liquids, gases or powders that are capable of flowing and that change shape at a steady rate when acted upon by a force tending to change its shape. Alternatively, one of the medicaments may be a solid that is carried, solubilized or otherwise dispensed with another fluid medicament.

This disclosed system is of particular benefit to users with dexterity or computational difficulties as the first variable input and second controlled/limited input (and the associated controlled therapeutic profile) removes the need for them to calculate their prescribed dose every time they use the device and this arrangement allows considerably easier setting and dispensing of the combined compounds.

In an embodiment of the proposed system, a master drug compound, such as insulin, is contained within a primary reservoir and a secondary medicament is contained within a secondary reservoir. Although Applicants' present patent application specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with Applicants' proposed system and method.

For the purposes of Applicants' system and method the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg (B32) human insulin; Lys(B3), Glu(B29) human insulin; Lys (B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-NH$_2$).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

One embodiment of Applicants' disclosure relates to a drug delivery system to deliver two or more medicaments through a single dispense interface, where the device has a housing containing a first user-operable dose setter operably connected to a primary reservoir of a first medicament containing multiple doses of at least one drug agent. The device also contains a second dose setting mechanism operably connected to a second reservoir of a second medicament containing multiple doses of at least one drug agent. A dose button is operably connected to the primary reservoir of medicament and a single dispense interface is configured for fluid communication with the primary reservoir. The secondary reservoir of a second medicament containing multiple doses of at least one drug agent is configured for fluid communication to the single dispense interface.

This dose button can be any type of mechanism that triggers the delivery procedure, whether driven mechanically or through a combination of electronics and mechanics. The button can move or be a touch sensitive virtual button, for example, a touch sensitive screen. Applicants' system has a single dispense interface configured for fluid communication with the primary reservoir and with a secondary reservoir of medicament containing at least one drug agent. The drug dispense interface can be any type of outlet that allows the two or more medicaments to exit the system and be delivered to the patient. Types of interfaces include hollow needles, catheters, atomizers, pneumatic injectors, or needle-less injectors, mouthpieces, nasal-applicators and the like interfaces.

The secondary reservoir preferably contains multiple doses of medicament but alternatively could also contain a single dose of medicament. As mentioned above, the system is designed such that a single activation of the dose button causes the user set dose of medicament from the primary reservoir and a non-user set dose of medicament from the second reservoir to be expelled through the single dispense interface. By user settable dose it is meant dose that the user (patient or health care provider) can physically manipulate the device to set a desired dose. Additionally, the user settable dose can be set remotely through the use of wireless communication (Bluetooth, WiFi, satellite, etc.) or the dose could be set by another integrated device, such as a blood glucose monitor after performing a therapeutic treatment algorithm. By non-user set dose it is meant that the user (or any other input) cannot independently set or select a dose of medicament from the secondary reservoir. In other words, when the user (or another input as described above) sets the dose of the primary medicament in the primary reservoir, the fixed dose of the second medicament is automatically set. However, in some examples, it may be possible for a user to adjust the device prior to setting a dose in order to alter the threshold dose where the fixed dose will be set.

In an example of Applicants' proposed system, a drug delivery device includes a variable dose setting mechanism, a fixed dose setting mechanism, a single dose setter, a collar, and a linkage component. The variable dose setting mechanism is operably coupled to a primary reservoir holding a first medicament. The fixed dose setting mechanism is operably coupled to a secondary reservoir holding a second medicament. Further, the single dose setter is operably coupled to the variable dose setting mechanism. Still further, the collar is disposed on the variable dose setting mechanism, and the linkage component is disposed on the fixed dose setting mechanism. The linkage component is capable of engagement with the collar.

In an example, the collar is a ring-shaped collar having a gap between a first end of the collar and the second end of the collar, wherein the collar comprises a groove, and wherein the linkage component comprises a pin that is slidably engageable with the groove. In another example, the collar comprises a groove having a plurality of sections, wherein a first section is a generally flat section and a second section is a helical section, and wherein the linkage component comprises a pin that is slidably engageable with the groove. In yet another example, the collar comprises a first section having a first groove projection and a second section having a second groove projection, wherein the linkage component is capable of engagement with the first groove projection after a first minimum dose of the first medicament is set, and wherein the linkage component is capable of engagement with the second groove projection after a second minimum dose higher than the first minimum dose is set. In one embodiment the collar comprises a groove and the linkage component comprises a flange that is slidably engageable with a groove.

In a further embodiment the collar may allow for variable stepped dose profile. The collar comprises a first section having a first groove projection and a second section having a second groove projection. For instance, the first section may be connected to the second section, and a connection arrangement between the two sections may be configured to allow adjusting the distance between the first and the second section, e.g. to increase the distance between the first section and the second section. In one embodiment the connection arrangement may comprise a male thread and a female thread.

Applicants' present disclosure also covers a method of dispensing a fixed dose of one medicament and a variable dose of another medicament from separate reservoirs that involves the steps of first setting a dose of a first medicament contained in a primary reservoir of a drug delivery device having a single dose setter. This setting of the first dose automatically sets the dose from a secondary reservoir (e.g., after a minimum first dose threshold is exceeded) without a separate input by the user. Next a dose button is activated that moves both the set dose of the first medicament from the primary reservoir and the automatically set non-user settable dose from the secondary reservoir through a single dispense interface.

The combination of compounds as discrete units or as a mixed unit can be delivered to the body via an integral needle. This would provide a combination drug injection system that, from a user's perspective, would be achieved in a manner that very closely matches the currently available injection devices that use standard needles. One possible delivery procedure would involve the following steps:

1. Attach a single dispense interface, such as a needle hub, to the distal end of the injection device such that the proximal end of the single dispense interface is in fluidic communication with both the first medicament and second medicament.
2. Dial up (i.e., set) the injection device such that it is ready to dispense the desired dose of the first medicament. As the single dose setter sets the dose of the first medicament, a predefined non-user settable dose of the second medicament is automatically set at the same time.
3. Insert or apply the distal end of the single dispense interface to the patient at or into the desired administration site. Dose the first medicament by activating a single dose button, which also causes the second medicament to automatically dispense.

The drug delivery system of Applicants' disclosure may be designed in such a way as to limit its use to exclusive primary and secondary reservoirs through employment of dedicated or coded features.

A particular benefit of Applicants' proposed system and method is that the use of two multi-dose reservoirs makes it is possible to tailor dose regimes when required, especially where a titration period is necessary for a particular drug. In an example, a set of drug delivery devices may be provided that have second dose setting mechanisms and/or reservoirs that have different properties, and thus result in different fixed doses of a second medicament. The drug delivery devices could be supplied in a number of titration levels with obvious differentiation features such as, but not limited to, aesthetic design of features or graphics, numbering etc, so that a user could be instructed to use the supplied drug delivery devices in a specific order to facilitate titration. Alternatively, the prescribing physician may provide the patient with a number of "level one" titration drug delivery devices and then when these were finished, the physician could then prescribe the next level.

A further feature of an example of Applicants' proposed system and method is that both medicaments are delivered via one injection needle and in one injection step. This offers a convenient benefit to the user in terms of reduced user steps compared to administering two separate injections. This convenience benefit may also result in improved compliance with the prescribed therapy, particularly for users who find injections unpleasant, or who have dexterity or computational difficulties. The use of one injection instead of two reduces the possibility for user errors and so may increase patient safety.

These as well as other advantages of various aspects of the present invention will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which:

FIGS. 4a-k illustrates another example drug delivery device in accordance with an example of Applicants' disclosure at various phases of the operation of the device;

DETAILED DESCRIPTION

Figure 1:
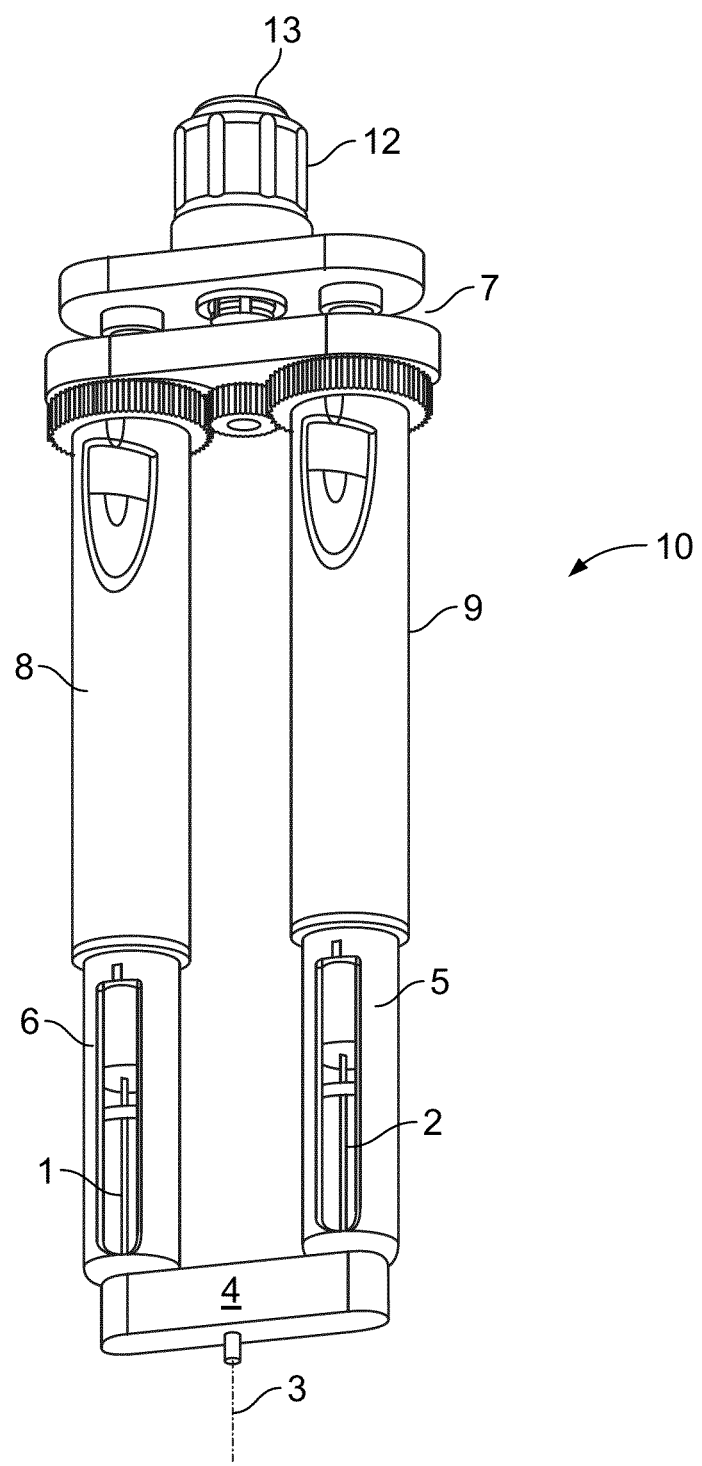
FIG. 1 illustrates an example drug delivery system, the drug delivery system having two multi-dose reservoirs positioned side-by-side containing a first medicament and a second medicament, respectively.
Figure 2:
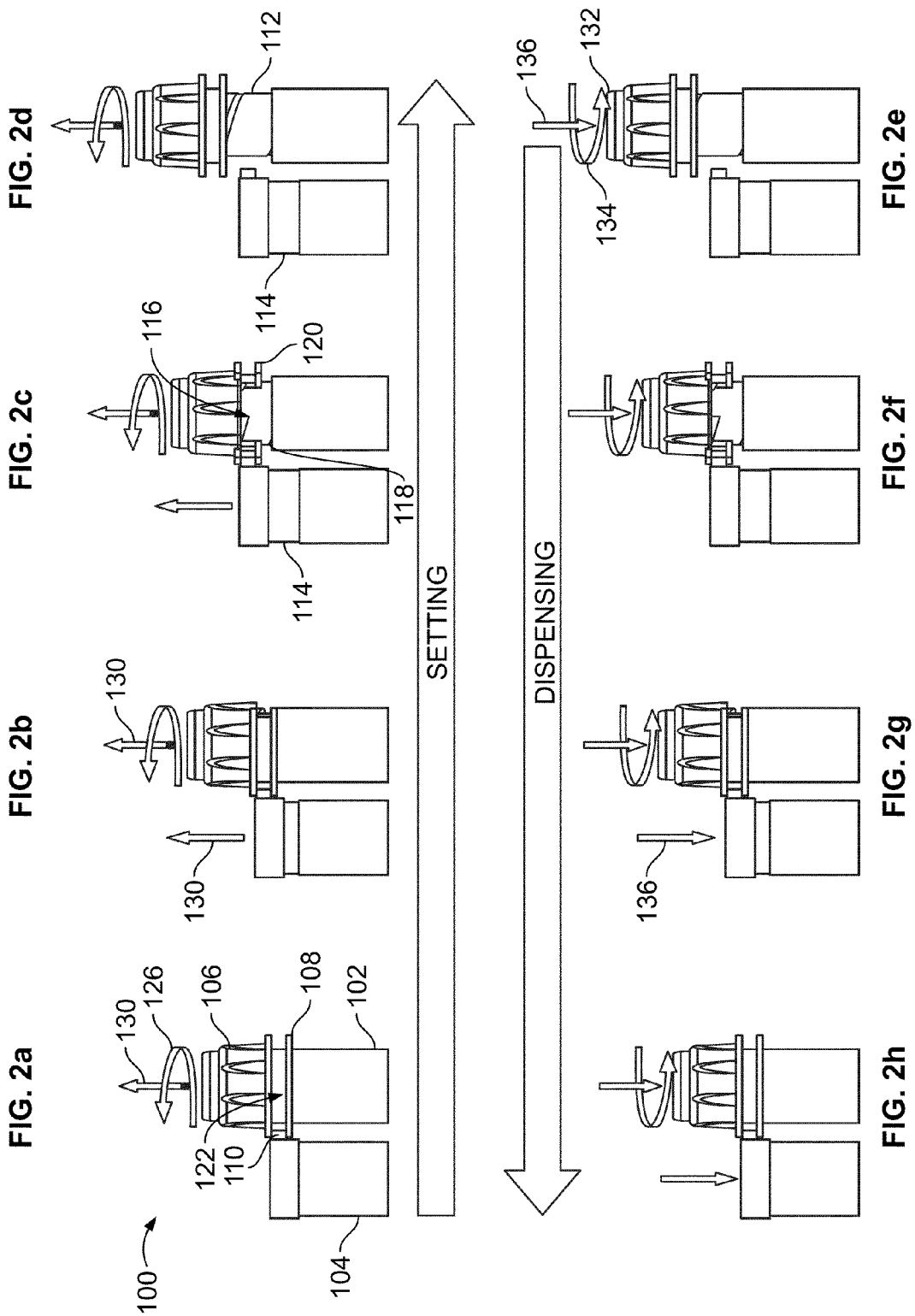
FIGS. 2a-h illustrates an example drug delivery device in accordance with an example of Applicants' disclosure at various phases of the operation of the device.

The drug delivery system of the present disclosure administers a variable dose of a first medicament (primary drug compound) and a fixed dose of a second medicament (secondary drug compound) through a single output or drug dispense interface. Setting the dose of the primary medicament by the user automatically sets the dose of the second medicament. In an example the drug dispense interface is a needle cannula (hollow needle). FIG. 1 generally illustrates a multi-dose injection device that is capable of setting and delivering both a dose of a first medicament and a second medicament via a single dose setter and a single dispense interface. The multi-dose injection device may include a mechanical link that links a variable dose setting mechanism to a fixed dose setting mechanism. According to an example of Applicants' proposed concept, the mechanical link may comprise a collar on the variable dose setting mechanism and a linkage component on the fixed dose setting mechanism. Example drug delivery devices having a collar disposed on the variable dose setting mechanism and a linkage component on the fixed dose setting mechanism are described with reference to FIGS. 2, 4, 8, 9 and 10. These example drug delivery devices are capable of achieving a wide variety of desired therapeutic dose profiles.

Returning to FIG. 1, FIG. 1 illustrates one possible example drug delivery system, where a multi-use injection device 10 has two reservoirs that are positioned side-by-side with one containing a first medicament 1 and the other a second medicament 2. These reservoirs may contain multiple doses of each medicament. Each reservoir may be self-contained and provided as sealed and sterile cartridges. These cartridges can be of different volumes and replaceable when empty or they can be fixed (non-removable) in the system. They can also have pierceable seals or septa to accept needle cannula.

The cartridges may be housed in cartridge holders 5 and 6 that have attachment means compatible with a removable, disposable hub or housing 4 that contains the single dispense interface. In this example the single dispense interface is shown as output needle 3. The hub can be of any design, provided that it allows for fluid communication between the primary and secondary medicaments and the single dispense interface or needle 3. An example design of hub 4 would include what is generally referred to in the art as a "2-to-1 needle" configuration. Although not shown, hub 4 could be supplied by a manufacturer contained in a protective and sterile capsule or container where the user would peel or tear open a seal or the container itself to gain access to the sterile single dispense interface. In some instances it might be desirable to provide two or more seals for each end of the hub. The seal may allow display of information required by regulatory labeling requirements. When a needle is used to deliver the medicaments it is preferred that the hub is designed to be economical and safe for allowing the user to attach a new hub for each injection. Attachment of hub 4 to the multi-use device 10 creates a fluid connection between output needle 3 and medicaments 1 and 2.

The example in FIG. 1 uses a rotational coupling 7 to mechanically link two dose delivery assemblies 8 and 9 in such a way that rotation of single dose setter 12 allows the user to select a dose of the primary medicament 1 and automatically set a fixed or predetermined non-user settable dose of secondary medicament 2. In the embodiment illustrated, the rotational coupling 7 has been embodied as a gear train in which counter-clockwise rotation of the single dose setter causes clockwise rotation of dose dial components (not shown) within the dose delivery assemblies 8 and 9. Rotational coupling 7 may be constructed such that it moves vertically at the same rate as both of the dial components. This allows it to set and dispense both drug compounds throughout the full operational range of the device.

As generally understood by those skilled in the art, it may be convenient to use lead screws or spindles to push on or drive a piston or bung contained within a cartridge of medicament. As such, spindles may be used in each dose delivery assembly. By varying the spindle pitches it is possible to vary the dose sizes (and dose ratio) in relation to each other. Specifically, this allows variation of the therapeutic profile to suit a specific therapy or patient requirements by providing devices with different dose ratios. The device shown in FIG. 1 could be operated as follows:

a. Counter-clockwise rotation of the dose setter 12 causes counter-clockwise rotation of the drive gear and clockwise rotation of both driven gears in rotational coupling 7. Clockwise rotation of both driven gears forces both dial components in dose delivery assemblies 8 and 9 to rotate in the same direction and follow a helical path out of the body of the device. This operation allows the user to set a target dose of medicament 1, but not medicament 2, which is automatically set by the dose selected for medicament 1.

b. Initiation of the dosing phase begins with the actuation of dispense or dose button 13. This causes the dial components to rotate independently of the dose setter.

c. During the dosing phase, the direction of rotation of the single dose setter as well the internal components of both device mechanisms is reversed. The rotational coupling 7 moves back towards the body of the device as both dial components wind back into the mechanisms following their respective helical paths. This reversal of rotation of both mechanisms coupled with the internal overhauling of the spindles by internal drive sleeves (not shown) causes both medicaments to be dispensed in a simultaneous fashion following the fixed ratio profile defined when the user set the target dose of medicament 1.

Varying the spindle pitches of the individual device mechanisms in relation to each other may alter the relationship of the fixed ratio of medicaments. Variation of the spindle pitch changes the advance of the spindle during dispense for a given amount of rotation during setting. Differing amounts of advance between the two mechanisms has the effect of creating different dispense ratios between the mechanisms. Variation of the spindle pitches may have the effect of extending the operational window of delivery device 10 in terms of the range of fixed ratios that can be achieved. This may also assist in keeping the spindle pitch in a range that allows resetting should the device be required to be reusable. This means that multiple pen injectors each having a different therapeutic profile can be manufactured. Specifically, this allows variation of the therapeutic profile to suit a specific titration regime and ultimately individual patient requirements.

The attachment means between hub 4 and cartridge holders 5 and 6 can be those known to those skilled in the art, including threads, snap locks, snap fits, luer locks, bayonet, snap rings, keyed slots, and combinations of such connections. The connection or attachment between the hub and the cartridge holder may also contain additional features (not shown), such as connectors, stops, splines, ribs, grooves, pips, clips and the like design features, that ensure that specific hubs are attachable only to matching drug delivery devices.

The shape of the dispense device 10, including hub 4, may be generally oval and/or cylindrical or any other geometric shape suitable for hand manipulation by a user. Additionally, hub 4 could incorporate a safety shield device that would prevent accidental needle sticks and reduce the anxiety experienced by users who suffer from needle phobia. The exact design of the safety shield is not critical to the drug delivery device, however, an example design is one that is operably connected to the first and/or second reservoirs. In such a design the activation of the safety shield could unlock the drug delivery system or instigate fluid communication between the reservoirs and in some cases cause the second medicament to be dispensed prior to activating the dose button to dispense the primary medicament from the first reservoir. Another example design would physically prevent insertion of the used drug dispense interface into the patient (e.g. a single use needle-guard type arrangement).

As mentioned an example design of Applicants' drug delivery device would include cartridges to contain the medicaments. Cartridges are typically cylindrical in shape and are usually manufactured in glass, sealed at one end with a rubber bung (piston) and at the other end by a rubber septum using a metal ferrule. The dose delivery assemblies are typically powered by a manual action of the user. However, the injection mechanism may also be powered by other means such as a spring, compressed gas or electrical energy.

A drug delivery device in accordance with Applicants' proposed concept may include a collar and a linkage component that mechanically link a variable dose setting mechanism and a fixed dose setting mechanism. FIGS. 2, 4, 8, and 9 depict various examples of such a mechanical link. In general, a drug delivery device in accordance with Applicants' disclosure may comprise (i) a variable dose setting mechanism, wherein the variable dose setting mechanism is operably coupled to a primary reservoir holding a first medicament, (ii) a fixed dose setting mechanism, wherein the fixed dose setting mechanism is operably coupled to a secondary reservoir holding a second medicament, (iii) a single dose setter operably coupled to the variable dose setting mechanism, (iv) a collar disposed on the variable dose setting mechanism, and (v) a linkage component disposed on the fixed dose setting mechanism, wherein the linkage component is capable of engagement with the collar. In an example, the variable dose setting mechanism is a rotationally-set dose setting mechanism and the fixed dose setting mechanism is an axially-set dose setting mechanism.

FIGS. 2a-h depict an example drug delivery device in accordance with an embodiment of Applicants' disclosure. In particular, FIGS. 2a-h depict a proximal end of drug delivery device 100 during setting and dispensing phases of operation. Drug delivery device 100 includes a first dose setting mechanism 102 and a second dose setting mechanism 104. The first dose setting mechanism 102 may be a variable dose setting mechanism that is operably connected to a first reservoir holding a first medicament, such as first reservoir 6 holding first medicament 1 shown in FIG. 1. First dose setting mechanism 102 may be a rotationally-set dose setting mechanism. Such dose setting mechanisms are generally known in the art. The second dose setting mechanism 104 may be a fixed dose setting mechanism that is operably connected to a second reservoir holding a second medicament, such as second reservoir 5 holding second medicament 2 shown in FIG. 1. Fixed dose mechanism 104 may be an axially-set dose setting mechanism (e.g., pull-to-set, push-to-dispense mechanism). Such dose setting mechanisms are generally known in the art.

The drug delivery device 100 also includes a single dose setter 106 that is operably coupled to the variable dose setting mechanism 102. A collar 108 is disposed on the variable dose setting mechanism 102 and a linkage component 110 is disposed on the fixed dose setting mechanism 104. In the example depicted, the linkage component is a pin. However, other types of components are possible, including but not limited to a flange element. The collar and pin arrangement between the dose setting mechanism 102, 104 may result in a desired dose profile, such as a profile that comprises a variable dose of the first medicament 1 and a delayed, fixed dose of the second medicament 2, such as that shown in FIG. 3.

The collar 108 may be disposed on the variable dose setting mechanism 102 at various locations. For example, in the example of FIG. 2, the collar 108 is attached to a dial sleeve 112. However, in another example, the collar 108 could be disposed on the dose setter 106 itself, such as on the distal end of the dose setter 106. As depicted, the collar 108 may be a ring-shaped collar having a gap 116 (see FIGS. 2c and 2f) between a first end 118 of the collar and the second end 120 of the collar. The ring shape may generally be any suitable ring shape, such as a circular ring shape, an oval ring shape, or generally any polygonal ring shape. The collar 108 may also comprise a groove 122, and the linkage component 110 may be slidably engageable with the groove 122. The pin may be fixed to a moving rack 114 of the axially-set fixed dose setting mechanism 104. The pin 110 interfaces with the collar 108 such that when the collar 108 is rotated and moved in the proximal direction by the setting action, the pin 110 (and consequently the moving rack 114) is pulled in the proximal direction, thus setting the fixed dose setting mechanism 104.

The setting and dispensing phases are depicted in detail in FIGS. 2a-h. In particular, FIGS. 2a-2d depict various points during setting of the drug delivery device 100, and FIGS. 2e-h depict various points during dispense. As shown in FIG. 2a, when a user begins to rotate the dose setter 106 in rotational direction 126, the pin 110 rides within the collar groove 122. Although depicted here as being disposed in the collar groove 122 in the starting position (i.e., pre-set position), in other examples, the pin may not be engaged with the collar groove 122 until after dose setting has begun.

FIG. 2b depicts further setting of the variable dose setting mechanism 102. As the dose setter 106 (and therefore the collar 108) is rotated, the dial sleeve 112 rises in proximal direction 130 to set the variable dose of the first medicament. The pin 110 is also pulled up in proximal direction 130, and this action begins to set the fixed dose of the second medicament 2.

When the pin is lifted to the set point of the fixed dose setting mechanism 104, the gap 116 in the collar 108 allows the pin to disengage from the groove 122. The set point of fixed dose setting mechanism 104 is shown in FIG. 2c. When the second medicament 2 is fully set, the collar rotates past the pin 110 to allow for further setting of the first medicament 1, as shown in FIG. 2d. In other words, higher doses of the first medicament 1 may be set after the pin disengages from the collar after the fixed dose of the second medicament 2 is set.

FIG. 2e depicts the beginning of the dispense process. In particular, the dispense process may begin when a user pushes dose button 132. This action causes the dose setter 106 (and therefore the collar 108) to rotate in rotational direction 134, which in turn causes movement of the dose setter 106 in distal direction 136. This movement in distal direction 136 may begin the dispense of the first medicament 1. As shown in FIG. 2f, as the dose setter 106 and collar 108 rotate back down during dispense of the first medicament, the collar groove 122 realigns with the pin 110 and thus reengages with the pin 110. Further movement in the rotational direction 134 and distal direction 136 causes the collar 108 to push against the pin 110 and move the pin in the distal direction 136 as the pin moves through groove 122, as shown in FIG. 2g. When the dose setter 106 is fully depressed back to its starting position (i.e., pre-set position), as shown in FIG. 2h, both the first medicament 1 and the second medicament 2 are fully dispensed.

Figure 3:
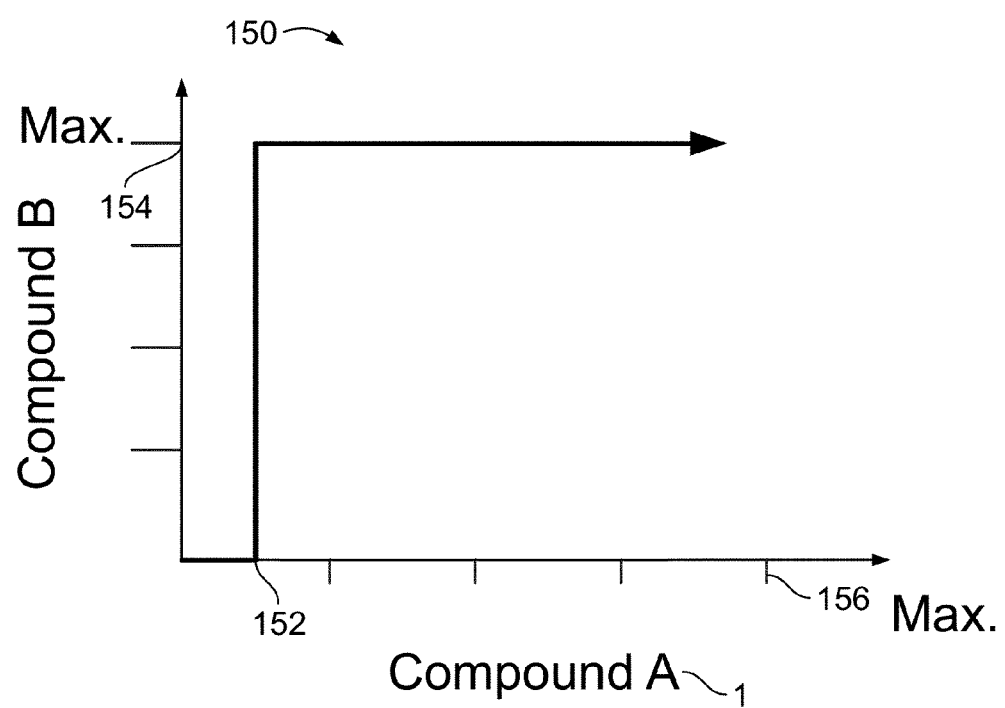
FIG. 3 illustrates an example possible dose profile achievable with the drug delivery device illustrated in FIG. 2.

Drug delivery device 100 may beneficially deliver a therapeutic dose profile that involves delivering a variable dose of a first medicament and delivering a fixed dose of a second medicament after a minimum dose of the first medicament is set. An example of such a profile is shown in FIG. 3. As seen in FIG. 3, profile 150 involves a fixed dose 154 of the second medicament 2 being set after a minimum variable dose 152 of the first medicament 1 is set. After the fixed dose 154 is set, the variable dose may be dialed further, such as up to a maximum dose 156.

For low dose settings of the first medicament 1 below the minimum threshold 152, the fixed dose setting mechanism does not reach its set point. In some examples, if this is the case, none of the second medicament would be dispensed. That is, the fixed dose setting mechanism 104 may be configured to only dispense medicament after a full fixed dose is set. Should a dose less than the full dose be set, the fixed dose setting mechanism may simply be configured to return to its starting position without dispensing a dose. Thus, the drug delivery device 100 beneficially may allow for priming of the device using just the first medicament 1. The device 100 may be particularly advantageous for examples where the second medicament 2 is particularly expensive compared to the first medicament 1. Since the fixed dose of the second medicament may not be set until a minimum dose of the first medicament 1 is set, the user may dial a priming dose (e.g., a dose less than dose 152) and prime solely with the first medicament.

A second example drug delivery device is shown in FIGS. 4a-k. In particular, FIGS. 4a-k depict a proximal end of drug delivery device 200 during setting and dispensing phases of operation. This drug delivery device 200 is similar in many respects to drug delivery device 100. For instance, drug delivery device 200 includes a first dose setting mechanism 202 operably connected to a primary reservoir holding a first medicament, such as first reservoir 6 holding first medicament 1. Drug delivery device 200 also includes a second dose setting mechanism 204 operably connected to a secondary reservoir holding a second medicament, such as second reservoir 5 holding second medicament 2. The drug delivery device 200 further includes a single dose setter 206 that is operably coupled to the variable dose setting mechanism 202. A collar 208 is disposed on the variable dose setting mechanism 202 and a linkage component 210 is disposed on the fixed dose setting mechanism 204.

These various components are generally the same as or similar to the corresponding components of drug delivery device 100; however, drug delivery device 200 has a modified collar 208 and a modified fixed dose setting mechanism 204. This modified collar 208 allows for achieving a modified therapeutic dose profile. Further, the modified fixed dose setting mechanism 204 allows for setting of a fixed dose that follows a stepped fixed dose profile. In other words, the fixed dose setting mechanism allows for the settable fixed dose to increase in increments based on the value of the dialed variable dose. Similar to the fixed dose mechanism 104, fixed dose setting mechanism 204 may be an axially-set fixed dose setting mechanism. As is generally known in the art, such devices may contain ratchet features to facilitate setting of a dose of medicament. In this case, additional ratchet features may be required to allow for half dose setting as well as full dose setting (described below). In a particular example, approximately 28 ratchet steps would be used; however, this number of ratchet steps can vary as needed. For example, having ratchet steps in multiples of 7 may be potentially beneficial as it relates directly to weeks, making planning for replacement prescriptions etc easier for a user. In one exemplary arrangement, Applicants' device may be configured such that the device has an additional, setting that facilitates priming. After this prime dose, the device is capable of delivering 14 further, 'complete' doses.

Figure 5:
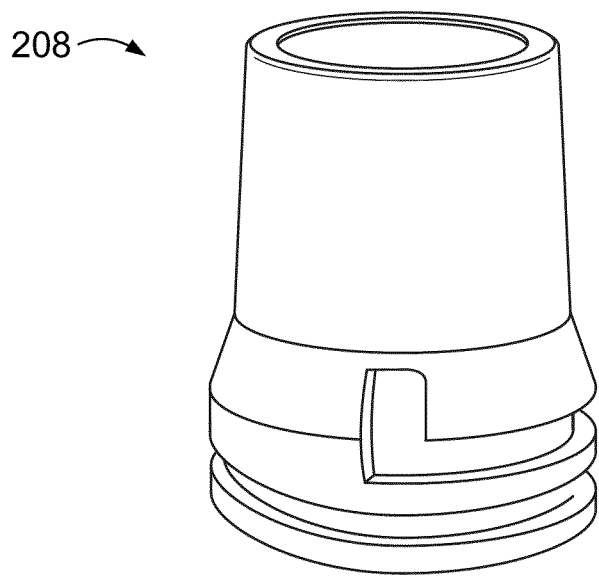
FIG. 5 illustrates a perspective view of collar of FIGS. 4a-c, where the collar is shown not yet disposed on a drug delivery device.

Specifically, the modified collar includes a groove having a plurality of sections. For example, the collar may comprise a groove having at least a first section that is a generally flat section and a second section that comprises a helical section. For instance, the collar 208 depicted in FIGS. 4a-k has a groove 222 that comprises four different sections. In particular, groove 222 has a first section 240, a second section 242, a third section 244, and a fourth section 246. The first section 240 and third section 244 are generally flat sections, whereas the second section 242 and fourth section 246 are helical sections. FIG. 5 illustrates a perspective view of collar 208, where the collar is shown not yet disposed on drug delivery device 200.

A collar such as collar 208 may beneficially achieve a stepped fixed dose profile. In particular, drug delivery device 200 may beneficially deliver a therapeutic dose profile that involves delivering a variable dose of a first medicament and delivering a stepped, fixed dose of a second medicament. For instance, a first fixed dose amount of the second medicament 2 may be set after a first minimum dose of the first medicament 1 is set, and a second fixed dose amount of the second medicament 2 may be set after a second minimum dose of the first medicament 1 is set. In an example, the collar 208 and fixed dose setting mechanism 204 may be configured to (i) set a half fixed dose of the second medicament 2 upon setting of a first minimum variable dose of the first medicament 1 and (ii) set a full fixed dose of the second medicament 2 upon setting of a second threshold dose of the first medicament 1. Such a profile is advantageous for certain therapies where it is beneficial for the dose of the second medicament 2 to increase in fixed stepped increments as the corresponding dose of the first medicament 1 increases. Each of these stepped increases only occurs once a specific predefined threshold dose of the first medicament 1 has been exceeded.

Figure 6A:
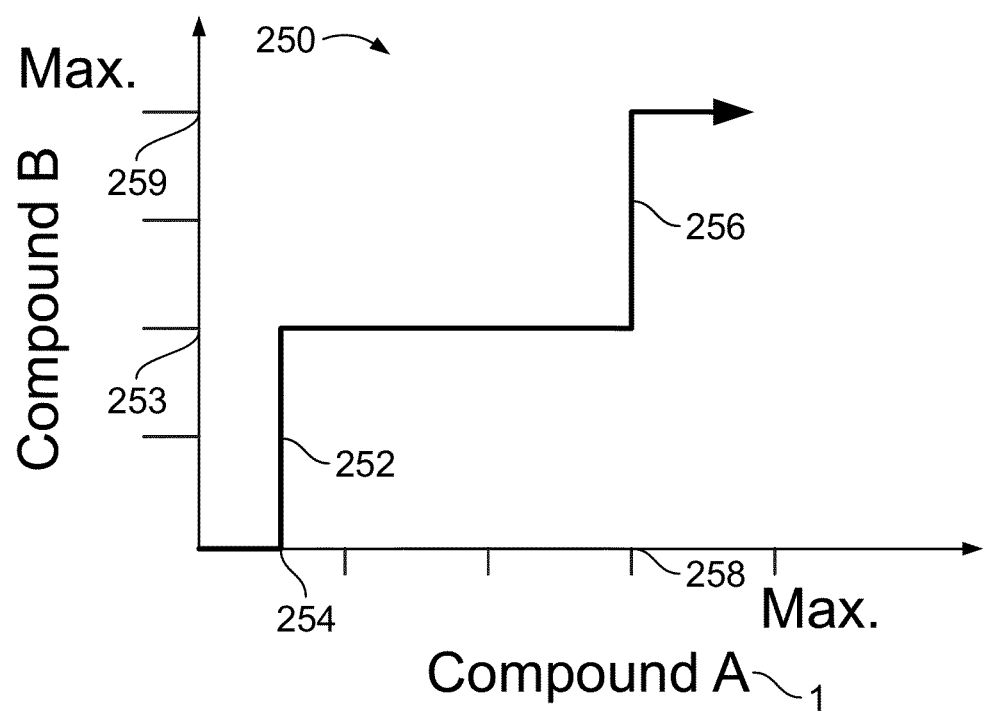
FIGS. 6a-c illustrate example possible dose profiles achievable with the drug delivery device illustrated in FIG. 4.
Figure 6B:
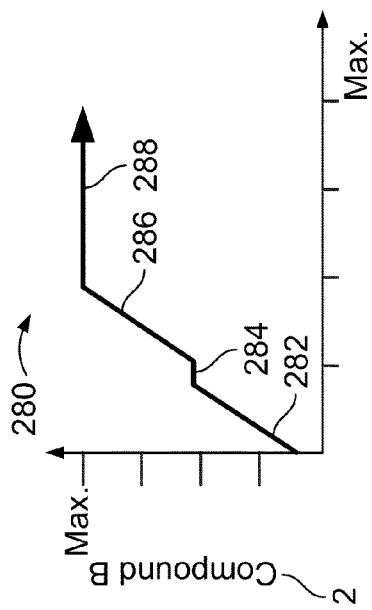
Figure 6C:
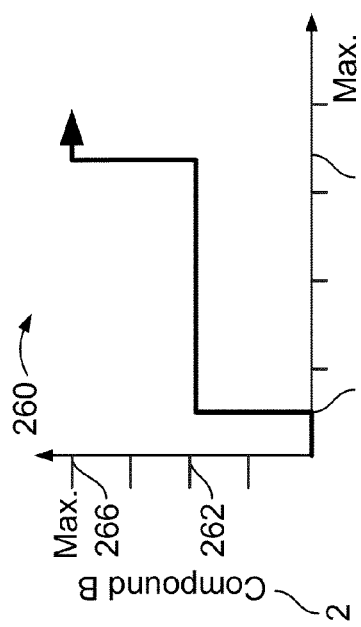

Various examples of such a stepped, fixed dose profile are shown in FIG. 6a-c. In the profile 250 shown in FIG. 6a, the first step 252 occurs when a threshold dose 254 of the first medicament 1 is set. The first step 252 results in a dose 253 of the second medicament 2 being set. In this example, the dose 253 is a half dose of the second medicament 2. However, it should be understood that the dose 253 could be any desired percentage of the second medicament 2. For example, this could be achieved by having non-uniform pitches (i.e., ratchet pitch for step 1 252 being different fro that pitch of step 2 256. The second step 256 occurs when a threshold dose 258 of the first medicament 1 is set. The second step 256 results in a dose 259 of the second medicament 2 being set. In this example, the dose 259 is a full (e.g., maximum) dose of the second medicament 2. However, it should be understood that the dose 259 could be any desired percentage of the second medicament 2. In this example, after the full dose 259 is set, the user may continue to set a higher dose of the first medicament 1. In addition, although only two steps are shown in this example dose profile, more steps are possible.

An example advantage of a drug delivery device such as drug delivery device 200 is the ability to define where the half and full set points (or any desired percentage) of the second medicament 2 occur relative to the setting of the first medicament 1. Potentially several variations of the drug delivery device could be manufactured and user prescribed to fit a variety of specific user needs. For example, a user who may typically use a high amount of the first medicament 1 may wish to split their dose (e.g., set and inject half a dose in one location and then set and inject the second half dose in another location) or may be required to split their dose to avoid injecting a high volume of medicament in a single location (which can, for example, cause discomfort). Such a user may benefit from the second threshold of the first medicament 1 (which determines when the full dose of the second medicament is set) being at a much higher point than their half dose of the first medicament, for example, in order to reduce the risk of overdosing the secondary medicament during split dose scenarios. An example of such a dose profile is shown in FIG. 6b. Dose profile 260 involves (i) setting a half dose 262 of the second medicament 2 upon setting of a variable dose 264 of the first medicament 1 and (ii) setting of the full dose 266 of the second medicament 2 upon setting of a variable dose 268 of the first medicament 1. As can be seen, the second threshold variable dose 268 is close to the maximum possible settable dose of the first medicament 1. Thus, a user who wishes to split injections may dial a half dose of the first medicament 1 (and deliver a half fixed dose of the second medicament with each half of their dose of the first medicament).

In another example, a user who may typically use a small amount of the first medicament 1 may ideally obtain their full dose of the second medicament 2 at their relatively low dose of the first medicament 1. The user may thus avoid the need for injecting more of the first medicament 1 than desired to obtain a full fixed dose of the second medicament 2. An example of such a dose profile is shown in FIG. 6c. Dose profile 270 involves (i) setting a half dose 272 of the second medicament upon setting of a low variable dose 274 of the first medicament and (ii) setting of the full dose 276 of the second medicament upon setting of a low variable dose 278 of the first medicament. Thus, a user does not have to dial nearly as high of a dose of the first medicament 1 to deliver a full fixed dose as in the example shown in FIG. 6b.

The setting and dispensing phases of drug delivery device 200 are depicted in detail in FIGS. 4a-k. In particular, FIGS. 4a-4e each depict various points during setting of the drug delivery device 200, and FIGS. 4f-k each depict various points during dispense. As shown in FIG. 4a, when a user begins to rotate the dose setter 206 in rotational direction 226, the pin 210 is in the collar groove 222 and, in particular, in the flat section 240 of the groove. As the dose setter 206 (and therefore the collar 208) is rotated, the dial sleeve 212 rises in proximal direction 230 to set the variable dose of the first medicament 1 and also forces the pin 210 to travel through the flat section 240. The pin may be fixed to a moving rack 214 of the axially-set fixed dose setting mechanism 204. The pin interfaces with the collar such that when the collar is rotated and moved in the proximal direction by the setting action, the pin (and consequently the moving rack) is pulled in the proximal direction, thus setting the fixed dose setting mechanism 204. With reference to FIG. 42b, as the pin travels through flat section 240, the fixed dose setting mechanism 204 also moves axially in proximal direction 230, thus beginning to set the fixed dose of the second medicament. This may set the half dose 253 of the second medicament 2 (see FIG. 6a).

As shown in FIG. 4c, after a given amount of movement in the proximal direction 230, the pin 210 enters the second/helical section 242. In this example, the helical section 242 is the same pitch as the dial sleeve of the variable dose setting mechanism and therefore results in the collar 208 rotating past the pin and not loading the fixed dose setting mechanism 204. In other words, as the pin 210 moves through the helical section 242, the fixed dose setting mechanism 204 does not move in the proximal direction 230.

After a given amount of rotation, the pin 210 enters the third/flat section 244, as shown in FIG. 4d. Further rotation then forces the pin 210 to travel through the flat section 244. With reference to FIG. 4e, as the pin travels through flat section 244, the fixed dose setting mechanism 204 also moves axially in proximal direction 230, thus setting the fixed dose of the second medicament 2. This may, for example, be the action that sets the full dose 259 of the second medicament (see FIG. 6a).

After the full fixed dose of the second medicament is set, the dose setter 206 may be rotated further to set a higher dose of the first medicament 1. In particular, when the pin 210 travels through the third, flat section 244, the pin then enters the fourth/helical section 246. In this section, the helical section 246 is the same pitch as the dial sleeve of the variable dose setting mechanism and so results in the collar 208 rotating past the pin and not loading the fixed dose setting mechanism. The pin may then exit the fourth, helical section 246 and the user can continue to set a higher dose of the first medicament, if desired.

In another example, the collar 208 may not include a fourth helical section. Rather, the collar may simply end at the third, flat section 244, and when the pin 210 exits this flat section, the dose setter could continue to be rotated to set a higher dose of the first medicament, if desired.

After setting the desired dose of the first medicament, the user may dispense the medicament. FIG. 4g depicts the beginning of the dispense process. In particular, the dispense process may begin when a user pushes dose button 232. This action causes the dose setter 206 (and therefore the collar 208) to rotate in rotational direction 234, which in turn causes movement of the dose setter 206 in distal direction 236. This movement in distal direction 236 may begin dispense of the first medicament 1. As shown in FIGS. 4g-h, as the dose setter 206 and collar 208 rotate back down during dispense of the first medicament 1, the pin 210 realigns with the flat section 244. Further movement in the rotational direction 234 and thus distal direction 236 causes the collar 208 to push against the pin 210 and move the pin in the distal direction 236 as the pin moves through the flat section 244. This action begins dispense of the second medicament 2. In the example where this flat section 244 increases the dose from a half dose to a full dose, half of the dose of the second medicament 2 will be dispensed as the pin travels through the flat section 244.

Further rotation forces the pin 210 to move through the helical section 242. Since the pitch matches that of the dial sleeve 212, the helical section winds back past the pin 210, and this action does not cause axial movement of the fixed dose setting mechanism in distal direction 236. However, the pin 210 then enters the flat section 240, as shown in FIGS. 4i-j, and this forces continued dispense of the second medicament 2. In the example where this flat section 240 sets the first half dose, that half of the dose of the second medicament will be dispensed as the pin travels through the flat section 240. When the dose setter 206 is fully depressed back to its starting position (i.e., pre-set position), as shown in FIG. 4k, both the first medicament 1 and the second medicament 2 are fully dispensed.

Beneficially, the groove sections can be modified in order to achieve a desired dose profile. For example, the groove may have more flat sections and more helical sections, and thus may result in more steps in the stepped, fixed dose profile. For instance, the groove sections could be designed such that the drug delivery device is capable of setting a ¼ dose, ½ dose, ¾ dose, and a full dose.

As another example, rather than having a flat section, the collar 208 may comprise a groove having (i) a first section that is a first helical section having a first pitch and (ii) a second section that is a second helical section having a second pitch different from the first pitch.

In yet another example, a drug delivery device having a collar may be configured to deliver medicament according to a dose profile that involves delivering a fixed ratio, a first fixed dose, an offset fixed ratio, and a second fixed dose. Similar to the example discussed above with respect to FIG. 4, a particular advantage of such a dose profile is the ability to define where the half and full set points (or any desired percentage) of the second medicament occur relative to the setting of the first medicament. Potentially several variations of the drug delivery device could be manufactured and user prescribed to fit a variety of specific user needs. For example, a user who may typically use a high amount of the first medicament may wish to split their dose (e.g., set and inject half a dose in one location and then set and inject the second half dose in another location) to avoid injecting a high volume of medicament in a single location (which can cause discomfort). Such a user may benefit from the second minimum threshold of the first medicament (which determines when the full dose of the second medicament is set) being at a higher point than their half dose of the first medicament.

Figure 7A:
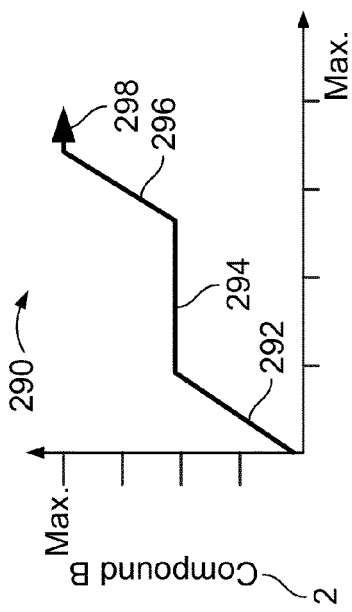
FIGS. 7*a-b* illustrate example possible dose profiles achievable with another drug delivery device in accordance with an example of Applicants' disclosure.
Figure 7B:
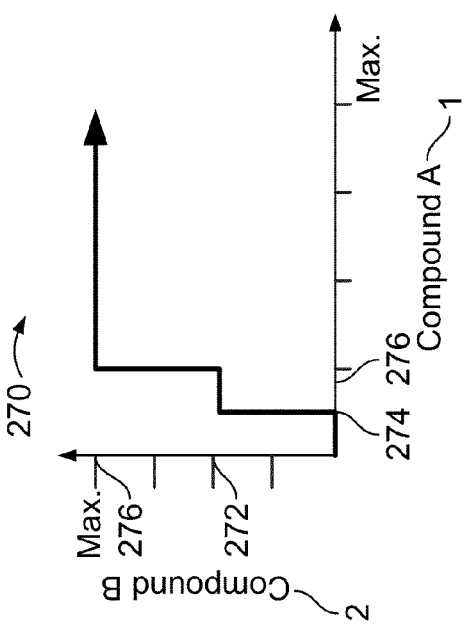

An example of a dose profile that involves a fixed ratio, a first fixed dose, an offset fixed ratio, and a second fixed dose is shown in FIG. 7a. Dose profile 280 involves a fixed ratio portion 282, a first fixed dose portion 284 of the second medicament 2, an offset fixed ratio portion 286, and a second fixed dose portion 288 of the second medicament 2. Another example of a dose profile that involves a fixed ratio, a first fixed dose, an offset fixed ratio, and a second fixed dose is shown in FIG. 7b. Dose profile 290 involves a fixed ratio portion 292, a first fixed dose portion 294, an offset fixed ratio portion 296, and a second fixed dose portion 298. Similar to the profile described with respect to FIGS. 6c, the example profile 280 may be useful for a low volume of first medicament user. Further, the example profile 290 may be useful for a high volume user of the first medicament.

Figure 8A:
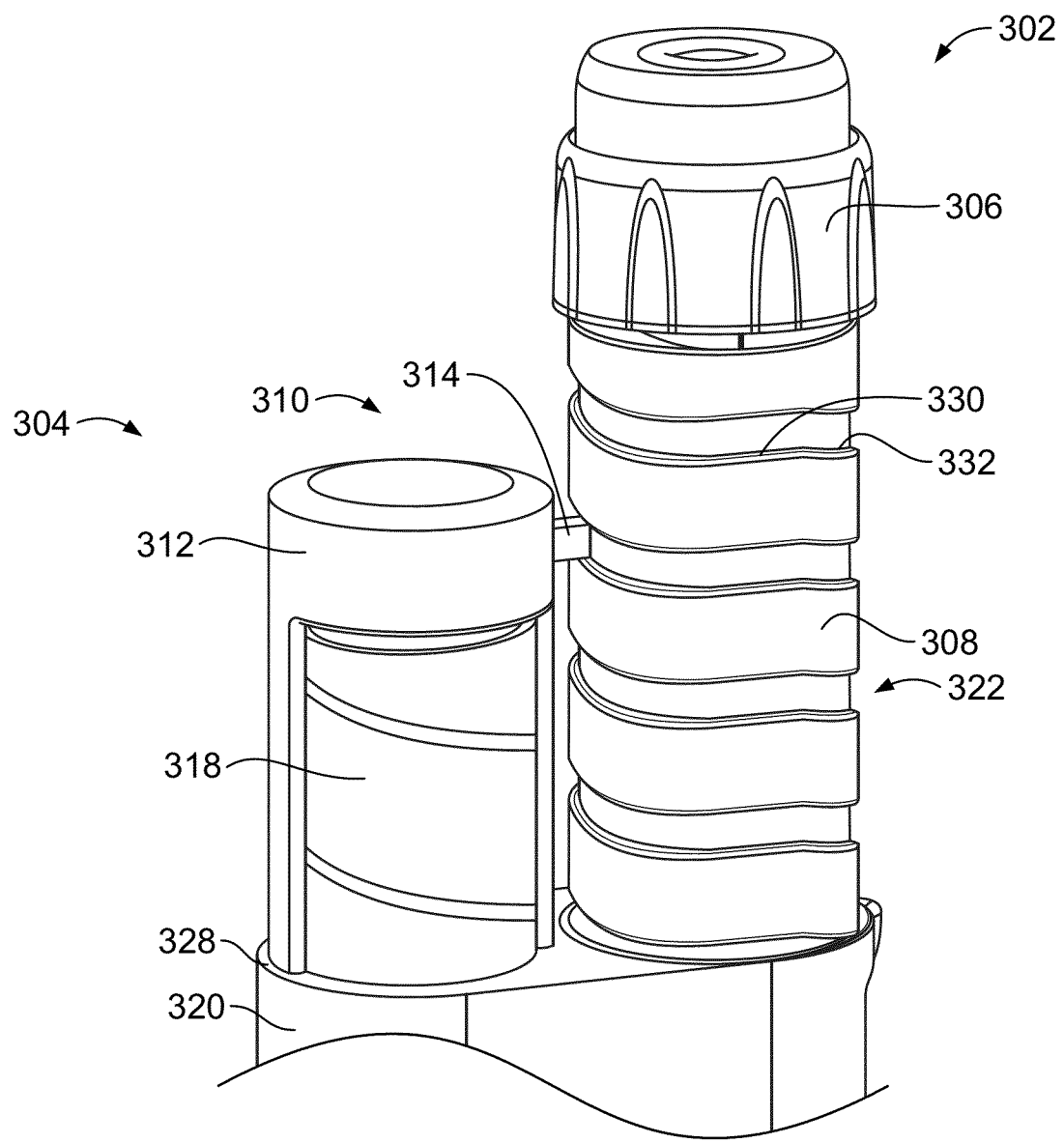
FIG. 8*a* illustrates an example drug delivery device in accordance with an example of Applicants' disclosure that is capable of achieving the example dose profiles of FIGS. 7*a-b*.
Figure 8B:
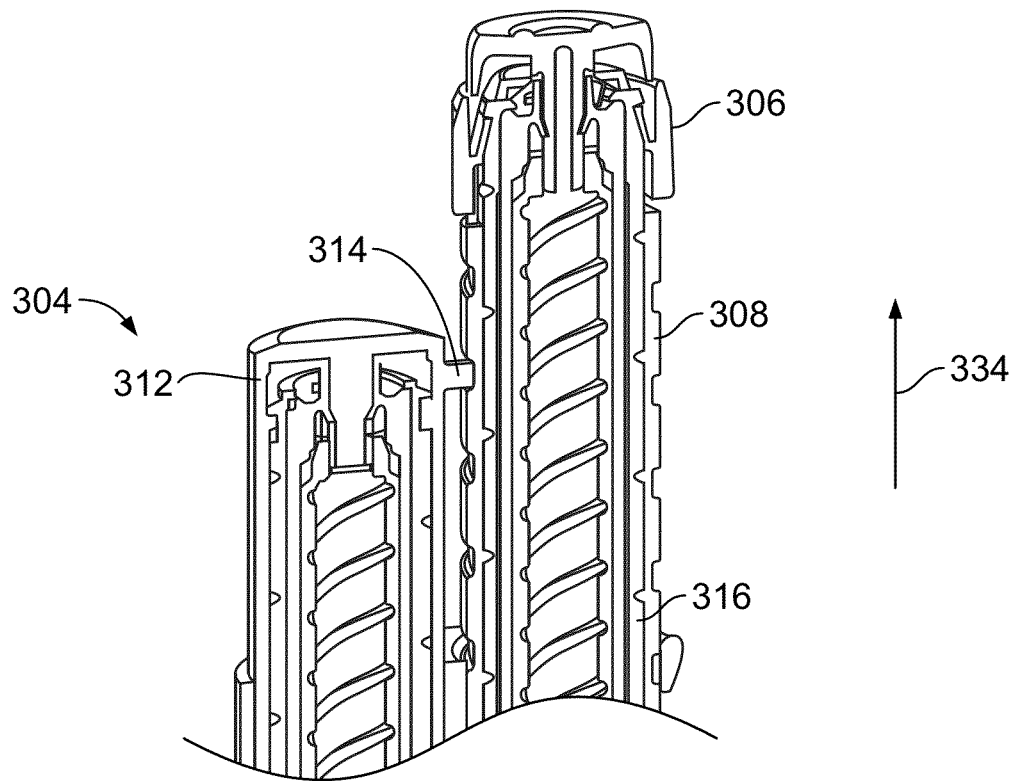
FIG. 8*b* illustrates a perspective cross-sectional view of the drug delivery device of FIG. 8*a* during dose setting.
Figure 8C:
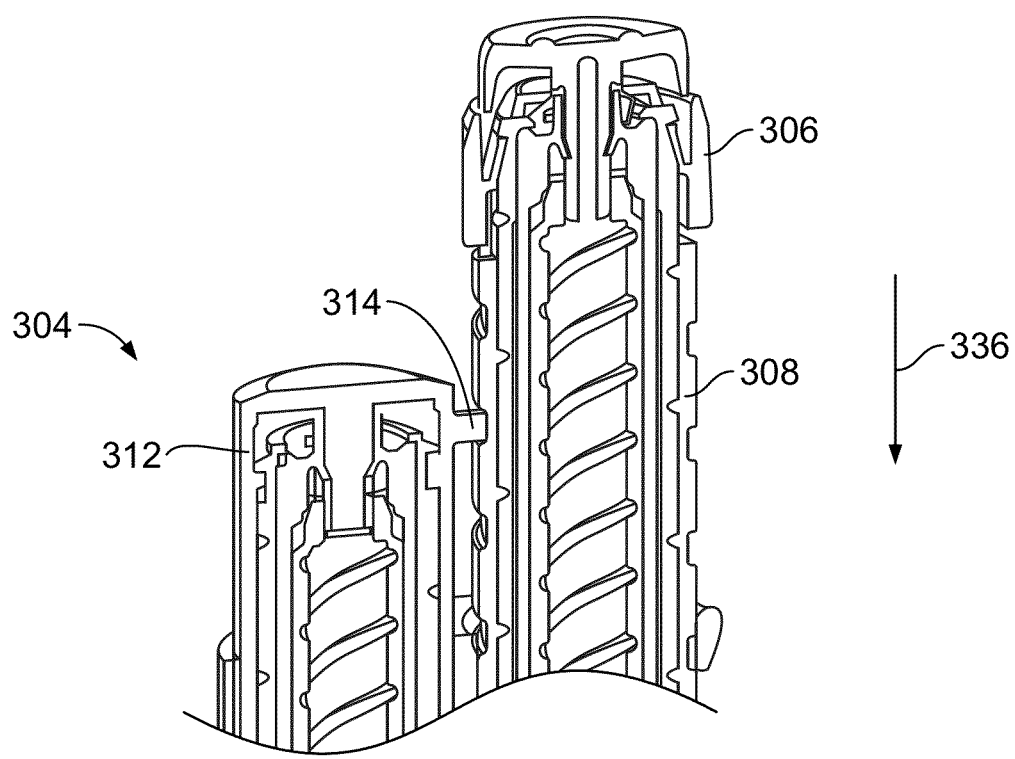
FIG. 8*c* illustrates a perspective cross-sectional view of the drug delivery device of FIG. 8*a* during dispense.
Figure 8D:
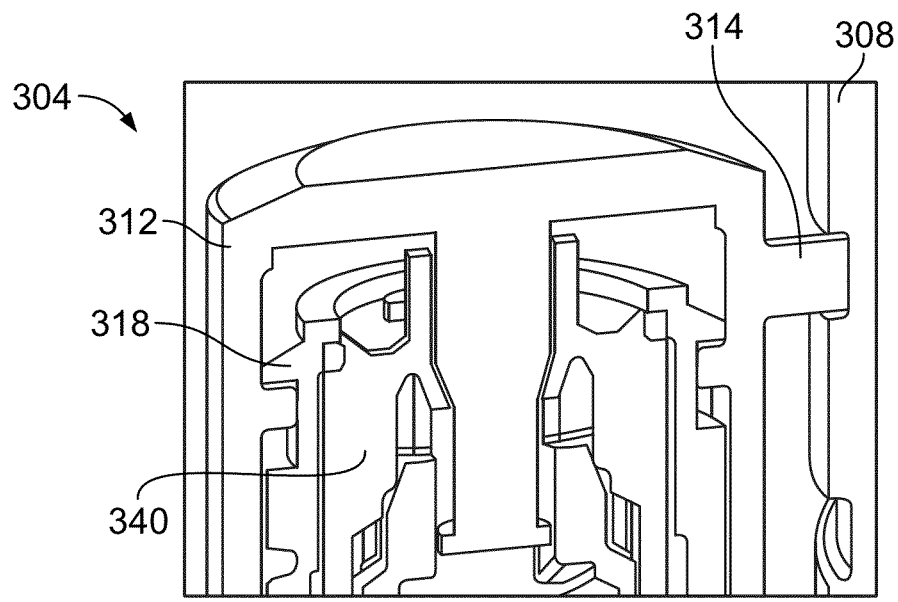
FIG. 8*d* illustrates a close-up view the fixed dose setting mechanism of the drug delivery device of FIG. 8*a*, where the clutch of the fixed dose setting mechanism is engaged.
Figure 8E:
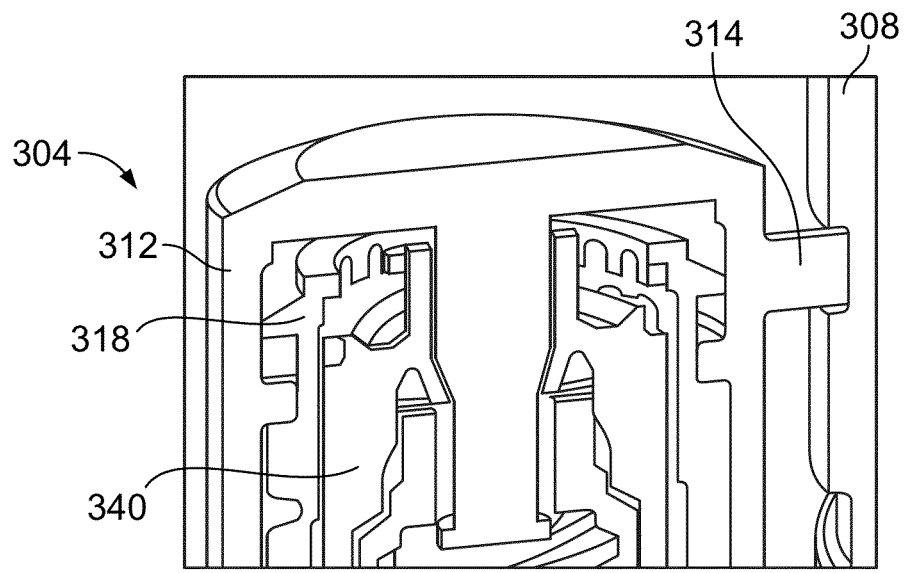
FIG. 8*e* illustrates a close-up view the fixed dose setting mechanism of the drug delivery device of FIG. 8*a*, where the clutch of the fixed dose setting mechanism is disengaged.

FIG. 8a depicts an example drug delivery device that may achieve a dose profile such as profile 280 or 290. Drug delivery device 300 is similar in many respects to drug delivery device 200 and thus is not described in as great of detail. For instance, drug delivery device 300 includes a first dose setting mechanism 302 operably connected to a primary reservoir holding a first medicament 1 and a second dose setting mechanism 304 may operably connected to a secondary reservoir holding a second medicament 2. The drug delivery device 300 also includes a single dose setter 306 that is operably coupled to the variable dose setting mechanism 302. A collar 308 is disposed on the variable dose setting mechanism 302 and a linkage component 310 is disposed on the fixed dose setting mechanism 304.

Compared to the fixed dose setting mechanism and linkage component of drug delivery device 200, however, the fixed dose setting mechanism and linkage component are slightly modified. In this example, the fixed dose setting mechanism 304 is a rotationally-set fixed dose setting mechanism. Further, the linkage component 310 comprises a pin sleeve 312 and a pin 314. The collar 308 is fixed to the dial sleeve 316 (see FIG. 8b) and/or dose setter 306, and the pin sleeve 312 and pin 314 are fixed relative to the dial sleeve 318 such that the pin sleeve 312 remains rotationally constrained fixed as the dial sleeve 318 rotates relative to the body 320 of the device 300. Dial sleeve 318 may or may not have the same pitch to that of dial sleeve 316. Rotational constraint for the pin sleeve 312 may be provided by engagement with engagement features on the body, such as leg feature 328. Similar to the examples described above, the pin sleeve 312 and pin 314 can impart lifting forces (for dose setting) or lowering forces (for dispense) to the second dose setting mechanism 304 via the pin 314 interaction with the collar 308.

Similar to collar 208, the collar 308 may comprise a groove 322 that has flat and helical sections. In particular, groove 322 has flat thread sections 330 and helical thread sections 332. As described above, the flat sections 330 result in the pin 314 being pulled upwards due to the dialing of dose setter 306. The helical sections 332 may be the same pitch as the dial sleeve 316 and so would result in the collar 308 rotating past the pin (and thus not loading the second medicament) as the dose setter 306 is rotated. In particular, with reference to FIGS. 8a-b, during dialing, when the pin 314 engages with the flat helical sections 330 on the collar 308, load is transferred to move the pin sleeve 312 (and hence the fixed dose setting mechanism 304) proximally in direction 334 at the same rate as the dose setter 306. However, when the pin 314 is located in the helical sections 332 of thread on the collar 308, no load is transferred and so no proximal movement of the fixed dose setting mechanism 304 occurs. Note that while FIG. 8a depicts five flat sections and five helical sections, more or fewer flat and helical sections are possible.

Since the fixed dose setting mechanism 304 is a rotationally-set fixed dose setting mechanism, the dose profile achieved when the pin 314 is lifted axially is a fixed ratio, as shown in FIGS. 7a-b.

On dispense, the helical sections 332 of the collar 308 will pass the pin 314 and the flat sections 330 will push down on the pin 314, resulting in dispense of the second medicament. With reference to FIGS. 8a and 8c-e, during a dispense stroke, when the pin 314 engages with the flat helical sections 330 on the collar 308, load is transferred to the pin sleeve 312. This action shifts the pin sleeve 312 distally a small distance in distal direction 336 to disengage the clutch 340 on this side of the mechanism (see FIG. 8e) before moving the fixed dose mechanism 304 distally at the same rate as the dose setter 306. When the clutch 340 is disengaged, part of the load applied to the dose setter 306 is transferred to dispense medicament from the fixed dose setting mechanism 304. As with dialling a dose, when the pin 314 is located in the helical sections 332 of thread, no load is transferred and so no distal movement of the fixed dose setting mechanism 304 occurs.

Figure 9:
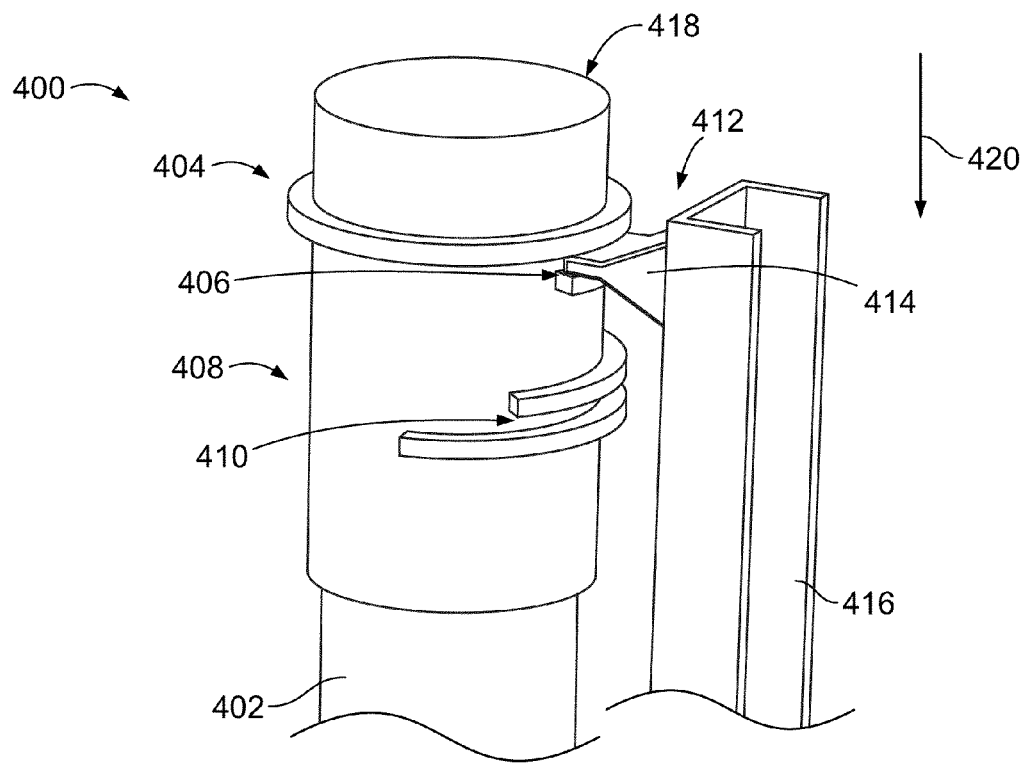
FIG. 9 illustrates components of another example drug delivery device in accordance with an example of Applicants' disclosure.
Figure 10:
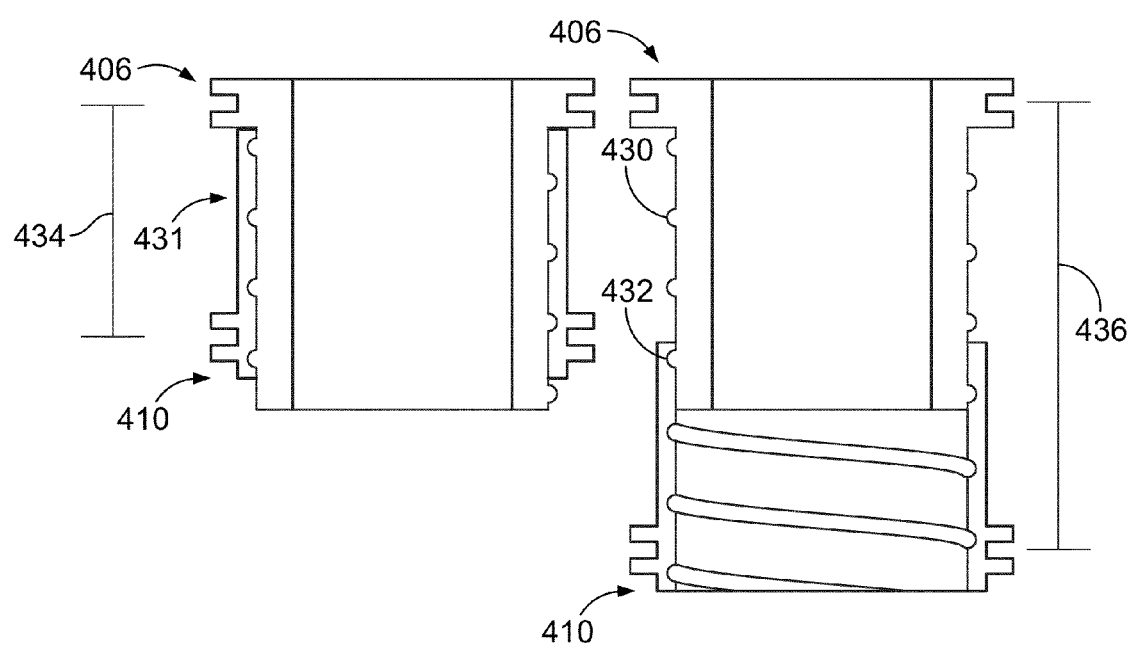
FIGS. 10*a-b* illustrate a cross-sectional view of another exemplary the collar of the drug delivery device of FIG. 9.
Figure 12:
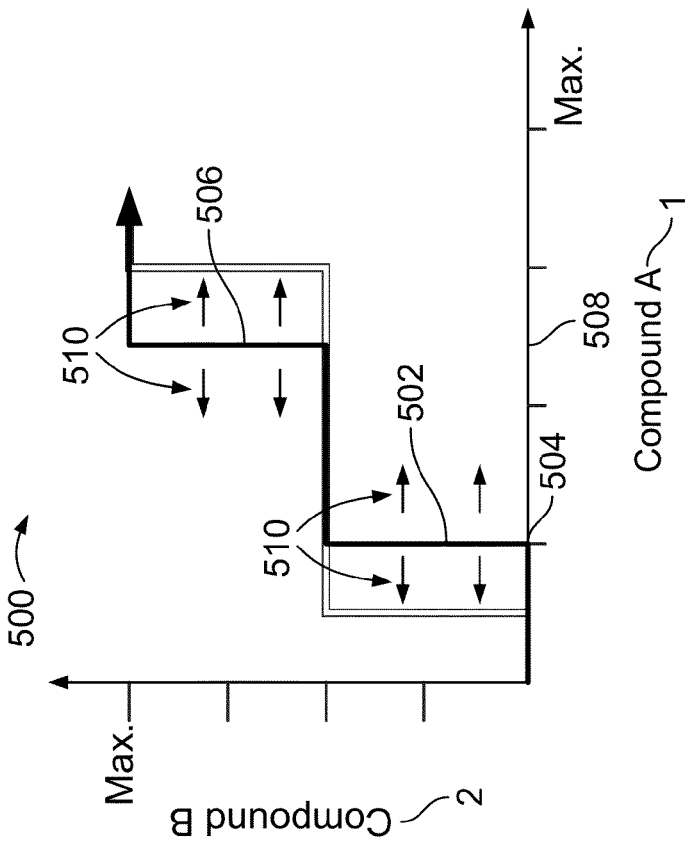
FIG. 12 illustrates another example possible dose profile achievable with the drug delivery device illustrated in FIG. 10*a-b*.

Another example collar for a drug delivery device in accordance with Applicants' proposed concept is shown in FIG. 9. This collar may also achieve a stepped dose profile, such as the stepped dose profile 250 shown in FIG. 6a. In addition, this collar may be capable of achieving a variable stepped dose profile. An example variable stepped dose profile is shown in FIG. 12. As seen in FIG. 12, in dose profile 500, the fixed dose of the second medicament increases in stepped intervals. Specifically, the first step 502 of the fixed dose (which in this example is a half dose) occurs when a threshold dose 504 of the first medicament is set, and the second step 506 of the fixed dose (which in this example complete the full fixed dose) occurs when a threshold dose 508 of the first medicament is set. However, the threshold doses where these steps occur may be varied in either direction, as indicated by arrows 510.

Returning to FIG. 9, the collar 400 is disposed on a first dose setting mechanism 402. The collar 400 comprises a first section 404 having a first grooved projection 406 and a second section 408 having a second groove projection 410. A second dose setting mechanism may comprise a linkage component 412. In the example of FIG. 9, the linkage component 412 comprises a flange 414 connected to a moving-rack component 416 of the second dose setting mechanism. The linkage component 412 is capable of engagement with the first groove projection 406 after a first minimum dose of the first medicament is set, and the linkage component is capable of engagement with the second groove projection 410 after a second minimum dose higher than the first minimum dose is set.

Operation of a device having a collar such as collar 400 is similar to the operation of the devices 100 and 200 described above. In particular, on rotation of the user interface 418, the variable dose setting mechanism 402 causes the collar 400 to rotate and move in proximal direction 420. As the collar 400 rotates, the flange 414 on the moving rack 416, which interfaces with the first groove projection 406 on the collar, is pulled in proximal direction 420, consequently beginning to set the second medicament 2.

When the first medicament 1 reaches a first predefined threshold, the first groove projection 406 ends. Consequently, as shown, there are no features on the collar 400 to interact with the flange 414. As a result, the first dose setting mechanism 402 can continue to rotate out (setting a higher dose of the first medicament) without pulling the moving rack 416 with the collar.

At a second predetermined point on the collar 400, a second groove projection 410 begins, such that the groove projection 410 engages the flange 414, causing the moving rack 416 to be pulled out further with continued dialing of the first medicament. It should be understood that the engagement with the groove projections is made possible by designing the collar appropriately. For example, the engagement may be made possible by designing the projections such that they follow a helical path which complements the rotation of the collar and ensures that the flange will be picked up as required on both dose selection and dispense.

Continuing to set the first medicament 1 will continue to pull the moving rack 416 until a complete fixed dose of the second medicament 2 is set. At this point, the second groove projection 410 could disengage, allowing a higher dose of the first medicament 1 to be set, if desired.

During dispense, the reverse occurs. That is, the projections 406, 410 rotate in the opposite direction but on the same helical path followed during dose setting. The collar 400 simultaneously rotates back into the housing of the device and engages with the flange 414 of the moving rack 416 at predetermined points in the dispense cycle. Whenever the flange 414 engages and the first medicament 1 is being dispensed, a step of the second medicament 2 will simultaneously be dispensed.

As mentioned above, in an example, the collar 400 may allow for a variable stepped dose profile. For instance, the first section may be connected to the second section, and a connection arrangement 431 between the two sections may be configured to allow adjusting the distance between the first and the second section, e.g. to increase the distance between the first section and the second section. An example connection arrangement 431 is shown in FIGS. 10a and 10b. This example connection arrangement allows for varying the distance between the first groove projection 406 and the second groove projection 410. In particular, the connection arrangement is a threaded arrangement, where the first section comprises a male thread 430 and the second section comprises a female thread 432. The threaded arrangement can be adjusted as desired to change the distance between the groove sections 406, 410. For example, FIG. 10a shows a distance 434 between groove projection 406 and groove projection 410, while FIG. 10b shows a distance 436 between groove projection 406 and groove projection 410. Other connection arrangements that may allow for varying the distance between the projections are also possible, including but not limited to a snap-fit type connection arrangement.

Figure 11A:
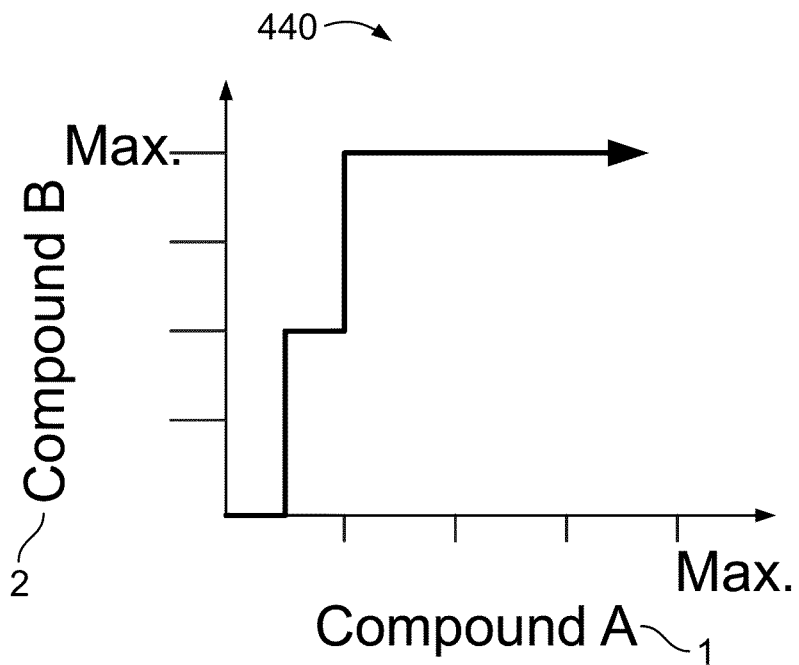
FIGS. 11*a-b* illustrate example possible dose profiles achievable with the drug delivery device illustrated in FIG. 10*a-b*.
Figure 11B:
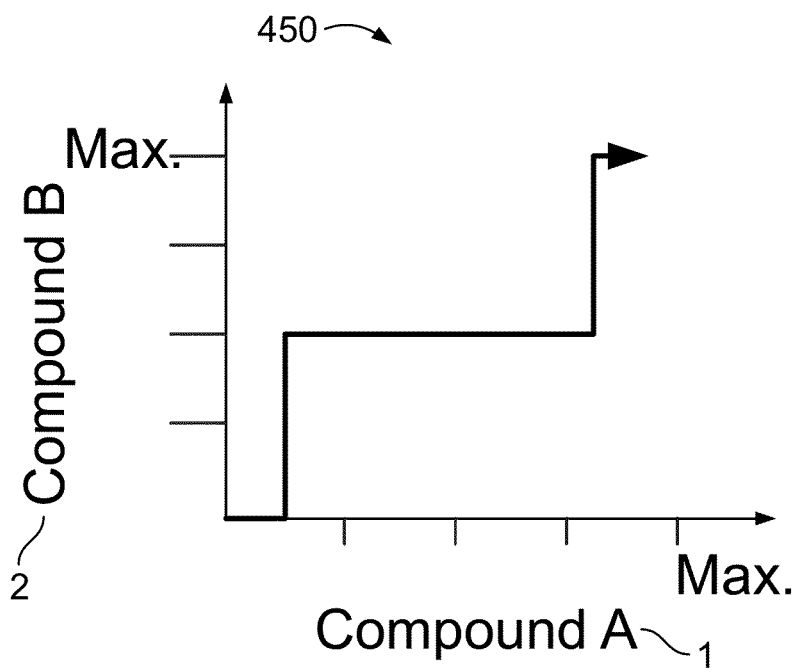

When the projections are close together, such as shown in FIG. 10a, the device may achieve a dose profile that involves a full dose of the second medicament being set at a relatively low threshold dose of the first medicament. For instance, a dose profile such as profile 440 (see FIG. 11a) may be achieved. However, where the projections are further apart, such as shown in FIG. 10b, the device may achieve a dose profile that involved a full dose of the second medicament being set at a higher threshold dose of the first medicament. For instance, a dose profile such as profile 450 (see FIG. 11b) may be achieved.

A benefit of this type of user variable interface is that the user may define the point at which the full dose of the second medicament 2 is set relative to the amount of the first medicament 1 that is set. This user variable interface could be a set-once arrangement, where a user (e.g., the patient or a healthcare professional) sets the distance between the grooved sections a single time. Alternatively, this user interface could be a feature that the user could adjust multiple times, as required. In either of these cases, it may not be necessary for the user to adjust this user interface before every injection. Therefore, the user steps required to perform the actual injection are simplified as the user is only required to operate the first user interface (i.e., the dose setter).

A further advantage of a drug delivery device having a collar such as collars 108, 208, 308, and 400 relates to the fact that the delayed setting of the second medicament means that a user may perform a priming step with only the first medicament (and not the second medicament). This priming can be carried out as many times as necessary (each with a volume up to the minimum threshold of the first medicament) without dispensing any of the second medicament. For a multi-dose drug delivery device, a profile of this type may, for example, be beneficial where (i) the second medicament dose not require repeated priming, (ii) the simultaneous priming of the first and second medicament might mask an unsuccessful priming of the first medicament, or (iii) the second medicament is a particularly expensive compound that preferably is not wasted. Other examples are possible as well.

In addition to increasing the distance between the first and second projections, the first set point (i.e., first minimum dose threshold) may be independently variable. Therefore, the point at which the second medicament begins to be set may be varied as desired.

For example, with reference to FIG. 9, this arrangement could be modified where the collar could be mounted onto a separate element (itself connected to the number sleeve or similar) via a helical thread such that rotation of the collar (and associated flanges) would move the connecting flange 406 distally relative to the pin 414. If the relationship between 406 and 410 were to be kept the same, then a part arrangement similar that in FIGS. 10a and b would be possible. If both the upper and lower steps were to be independently adjustable then an at least a three component sub-assembly arrangement would probably be required.

As described above, prior to each dose, the user could potentially vary the threshold at which the full dose of the second medicament is set, or the user may leave the threshold unchanged from its previously set value. Similarly, the half dose threshold could also potentially be varied by a user or by a prescribing healthcare professional prior to handover of the device.

As mentioned above, in some examples of the drug delivery devices described above, the device could be configured to have the fixed dose increase in a plurality of steps, such as two or more steps, each of which is set when an associated defined threshold of the first medicament is set.

In the example drug delivery devices described above, the drug delivery device may further include force-assist element to assist with dispense of at least one of the first medicament and the second medicament, such as a biasing element that assists with delivery of the medicament. The biasing element may be any suitable energy-storage element, such as but not limited to a constant force spring, a compression spring, a tension spring, and a torsion spring. In an example, during setting of the first and second medicament, energy may be added to the spring element, and during dispense this stored energy may be released to assist with the dispense of the medicament. For instance, when the spring element is operably coupled to the fixed dose setting mechanism, the spring element may assist with the dispense of the second medicament. By assisting with the dispense, the spring element may beneficially lower the force required from a user to dispense the medicament.

Figure 13A:
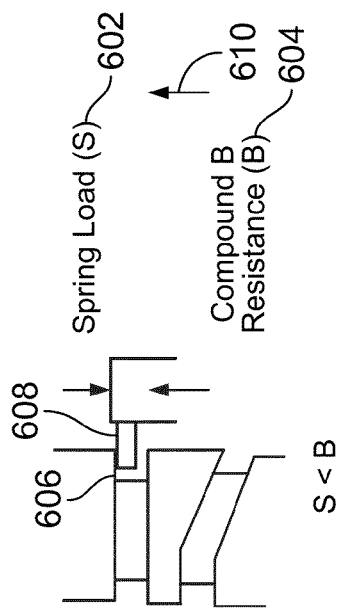
FIGS. 13*a-c* illustrates various examples of possible spring assist force for drug delivery devices in accordance with examples of Applicants' disclosure.

A particular characteristic of using a spring dispense assist element in conjunction with the example pin/collar arrangements of Applicants' disclosure is that at low spring force relative to the resistance of the second medicament dose setting mechanism during dispense, causes the collar to push against the pin. This increases frictional load, and therefore increases the user input force required to dispense medicament. This situation is depicted in FIG. 13a. As shown, spring force 602 ("S") is less than the resistance force 604 of the second dose setting mechanism ("B"). Therefore, the pin 608 applies an axial load against the collar 606 in proximal direction 610.

When the spring force is high relative to the resistance of the second medicament dose setting mechanism during dispense, the pin applies an axial load against the collar in distal direction 612. This situation is depicted in FIG. 13c. As shown, spring force 602 ("S") is greater than the resistance force 604 of the second dose setting mechanism ("B"). Therefore, the pin 608 pushes against the collar 606 in distal direction 612.

Figure 13B:
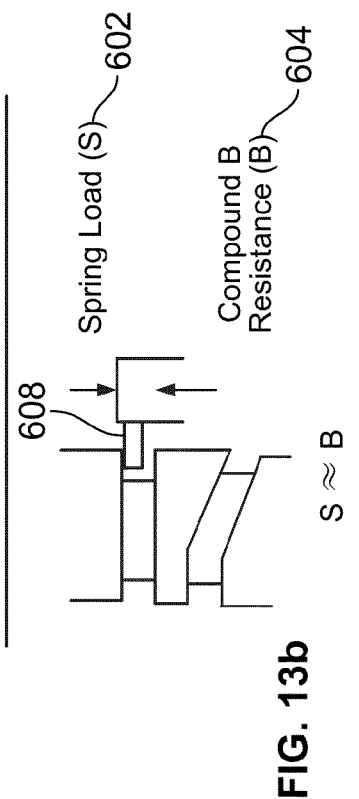
Figure 13C:
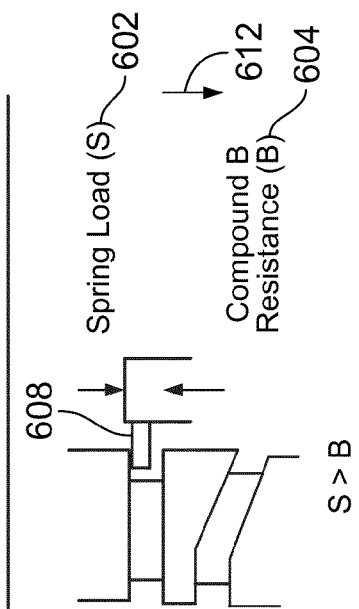

There may be a given balance where the spring force exactly equals the second dose setting mechanism resistance to movement, as depicted in FIG. 13b; however, as this is likely to be variable along the dispense stroke, achieving this given, ideal balance may in certain circumstances be difficult. However, a spring force can be incorporated such that the user load is increased slightly at a low second dose setting mechanism resistance and decreased at high resistance, thus evening out the user input force over the dispense stroke and lowering the peak force.

The disclosed drug delivery devices may be suited towards a modular disposable or re-usable platform in terms of managing drug wastage. This is because there is a risk of one medicament being finished before the other unless there is a strict 1:1 ratio between the two medicaments. However, where each side is resettable, new medicament reservoirs can be inserted and the device can continue to be used. Possible embodiments for a modular disposable platform could involve, but are not limited to, the replacement of the entire device mechanism fitted with a new primary pack. Suitable re-engagement features may be integrated into the device platform to facilitate the alignment and fastening of the individual device mechanisms together in a robust and user friendly fashion. It is possible that such features could be arranged to define the permissible functionality of the two individual elements on their own.

A possible re-usable platform would feature spindles that could be back wound into their respective devices once they had reached the limits of travel, such as those known in the art. In addition to this functionality, the platform would feature a means of replacing the medicament reservoir or reservoirs after the resetting of one or both spindles.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A drug delivery device comprising:
   a variable dose setting mechanism wherein the variable dose setting mechanism is operably coupled to a primary reservoir holding a first medicament;
   a fixed dose setting mechanism, wherein the fixed dose setting mechanism is operably coupled to a secondary reservoir holding a second medicament;
   a single dose setter operably coupled to the variable dose setting mechanism;
   a collar disposed on the variable dose setting mechanism;
   a linkage component disposed on the fixed dose setting mechanism, wherein the linkage component is configured to engage the collar,
   wherein the collar and the linkage component mechanically link the variable dose setting mechanism and the fixed dose setting mechanism,
   and wherein the drug delivery device is operable such that as a the single dose setter sets a variable dose of the first medicament, a pre-defined non-user settable dose of the second medicament is automatically set at the same time upon a minimum dose is exceeded.

2. The drug delivery device of claim 1, wherein the linkage component is capable of disengaging from the collar after the fixed dose is set.

3. The drug delivery device of claim 1, wherein the variable dose setting mechanism is a rotationally-set dose setting mechanism, and wherein the fixed dose setting mechanism is an axially-set dose setting mechanism.

4. The drug delivery device of claim 1, further comprising a force-assist element to at least assist with dispense of at least one of the first medicament and the second medicament.

5. The drug delivery device of claim 1, wherein the collar is a ring-shaped collar having a gap between a first end of the collar and the second end of the collar, wherein the collar comprises a groove, and wherein the linkage component comprises a pin that is slidably engageable with the groove.

6. The drug delivery device of claim 5, wherein the fixed dose setting mechanism comprises an axially movable rack coupled to the pin, and
wherein, during dose setting, rotation of the collar forces the pin to move through the groove and the axially moveable rack to lift in a proximal direction.

7. The drug delivery device of claim 5, wherein the drug delivery device is configured for delivering medicament according to a dose profile.

8. The drug delivery device of claim 1, wherein the collar comprises a groove having a plurality of sections, wherein a first section comprises at least one generally flat section and wherein a second section comprises at least one helical section, and wherein the linkage component comprises a pin that is slidably engageable with the groove.

9. The drug delivery device of claim 8, wherein the fixed dose setting mechanism comprises an axially movable rack coupled to the pin, and
wherein, during dose setting, rotation of the collar forces the pin to move through the groove and the axially moveable rack to lift in a proximal direction.

10. The drug delivery device of claim 8, wherein the drug delivery device is capable of delivering medicament according to a dose profile, wherein the dose profile is a stepped fixed dose profile.

11. The drug delivery device of claim 1, wherein the collar comprises a groove having a plurality of sections, wherein a first section is a first helical section having a first pitch, and wherein a second section is a second helical section having a second pitch different from the first pitch.

12. The drug delivery device of claim 1, wherein the collar comprises a groove having a plurality of sections, wherein a first section is a generally flat section and wherein a second section is a helical section, and wherein the linkage component comprises a pin sleeve and a pin that is slidably engageable with the groove.

13. The drug delivery device of claim 12, wherein the drug delivery device is capable of delivering medicament according to a dose profile, wherein the dose profile comprises a fixed ratio section, a first fixed dose section, an offset fixed ratio section, and a second fixed dose section.

14. The drug delivery device of claim 1, wherein the collar comprises a first section having a first groove projection and a second section having a second groove projection, and wherein the linkage component is capable of engagement with the first groove projection after a first minimum dose of the first medicament is set, and wherein the linkage component is capable of engagement with the second groove projection after a second minimum dose higher than the first minimum dose of the first medicament is set.

15. The drug delivery device of claim 14, wherein the first section is connected to the second section, and wherein a connection arrangement between the two is configured to allow adjusting the distance between the first section and the second section.

\* \* \* \* \*